US008206393B2

(12) United States Patent
Raus et al.

(10) Patent No.: US 8,206,393 B2
(45) Date of Patent: Jun. 26, 2012

(54) SURGICAL INSTRUMENT (75) Inventors: Laura Raus, Rome (IT); Fabrizio Caroli, Rome (IT); Peter Schulz, Löffingen (DE); Theodor Lutze, Balgheim (DE); Dieter Weisshaupt, Immendingen (DE); Markus Nesper, Tuttlingen (DE); Konstantin Faulhaber, Frittlingen (DE)

(73) Assignee: Laura Raus, Rome (IT)

( * ) Notice: Subject to any disclaimer, the term of this patent is extended or adjusted under 35 U.S.C. 154(b) by 1197 days.

(21) Appl. No.: 11/664,439

(22) PCT Filed: Sep. 27, 2005

(86) PCT No.: PCT/EP2005/010395
§ 371 (c)(1),
(2), (4) Date: Sep. 24, 2007

(87) PCT Pub. No.: WO2006/037510
PCT Pub. Date: Apr. 13, 2006

(65) Prior Publication Data
US 2008/0027448 A1 Jan. 31, 2008

(30) Foreign Application Priority Data
Oct. 1, 2004 (DE) .......................... 10 2004 049 243

(51) Int. Cl.
*A61B 17/32* (2006.01)
(52) U.S. Cl. .......................................... 606/83; 606/171
(58) Field of Classification Search ...... 30/43.91–43.92, 30/182, 208–210, 241, 392–394, 402; D24/146; 81/57.19, 57.21, 128–129; 83/533–537; 606/79–85, 86 R, 87, 167–189
See application file for complete search history.

(56) References Cited

U.S. PATENT DOCUMENTS

| | | | |
|---|---|---|---|
| 2,625,682 A | 1/1953 | Cristiano | |
| 2,740,406 A | 4/1956 | Tofflemire | |
| 2,751,940 A | 6/1956 | Miller | |
| 2,943,524 A | 7/1960 | Bourne | |
| 2,948,174 A | 8/1960 | Bourne | |
| 3,752,161 A * | 8/1973 | Bent | 606/184 |
| 3,913,585 A | 10/1975 | Wolvek | |
| 4,020,555 A * | 5/1977 | Hedrick | 30/392 |
| 4,522,206 A | 6/1985 | Whipple et al. | |
| 4,530,357 A | 7/1985 | Pawloski et al. | |
| 4,705,038 A * | 11/1987 | Sjostrom et al. | 606/180 |
| 4,848,338 A | 7/1989 | De Satnick | |
| 5,273,519 A | 12/1993 | Koros et al. | |
| 5,569,258 A | 10/1996 | Gambale | |
| 5,582,618 A * | 12/1996 | Chin et al. | 606/170 |
| 6,110,177 A * | 8/2000 | Ebner et al. | 606/84 |
| 6,322,579 B1 * | 11/2001 | Muller | 606/205 |
| 6,351,659 B1 | 2/2002 | Vilsmeier | |
| 6,575,977 B1 * | 6/2003 | Michelson | 606/83 |
| 6,599,291 B1 | 7/2003 | Foley et al. | |
| 2003/0216740 A1 | 11/2003 | Michelson | |
| 2003/0225411 A1 | 12/2003 | Miller | |
| 2004/0006335 A1 | 1/2004 | Garrison | |
| 2008/0027448 A1 | 1/2008 | Raus et al. | |

FOREIGN PATENT DOCUMENTS

| | | |
|---|---|---|
| DE | 3729513 | 3/1988 |
| WO | 02/34144 | 5/2002 |
| WO | WO 02062240 A1 * | 8/2002 |
| WO | 2004/086988 | 10/2004 |

OTHER PUBLICATIONS

Non-final Office Action issued by the USPTO for U.S. Appl. No. 10/551,721 dated Jan. 22, 2010.
Non-final Office Action issued by the USPTO for U.S. Appl. No. 10/551,721 dated Jan. 26, 2009.
Final Office Action issued by the USPTO for U.S. Appl. No. 10/551,721 dated Nov. 4, 2008.
Non-final Office Action issued by the USPTO for U.S. Appl. No. 10/551,721 dated May 13, 2008.
Final Office Action issued by the USPTO for U.S. Appl. No. 10/551,721 dated Jul. 8, 2010.
Notice of Allowance issued by the USPTO for U.S. Appl. No. 10/551,721 dated Aug. 25, 2010.
PCT International Search Report for PCT/EP2005/010395 filed on Sep. 27, 2005 in the name of Aesculap AG & Co. KG.
PCT International Written opinion for PCT/EP2005/010395 filed on Sep. 27, 2005 in the name of Aesculap AG & Co. KG.
PCT International Search Report for PCT/IT2003/000205 filed on Apr. 4, 2003 in the name of Fabrizio Caroli.

* cited by examiner

*Primary Examiner* — Thomas C. Barrett
*Assistant Examiner* — Larry E Waggle, Jr.
(74) *Attorney, Agent, or Firm* — Steinfl & Bruno, LLP (57) ABSTRACT

A surgical instrument for removing bone, cartilage, or similar tissue is described. The surgical instrument has a shaft that extends in a longitudinal direction and supports a cutting plate which is inclined perpendicular or relative to the longitudinal direction, and a cutting element which is movably mounted on the shaft and supports a blade at the distal end in which the blade is pointing in the direction of the cutting plate and being advanced to the cutting plate in order to cut tissue.

15 Claims, 7 Drawing Sheets

SURGICAL INSTRUMENT

CROSS REFERENCE TO RELATED APPLICATIONS

The present application is the US national stage of International Application PCT/EP2005/10395 filed on Sep. 27, 2005, which, in turn, claims priority to German Patent Application DE 102004049243.3 filed on Oct. 1, 2004.

FIELD

The present invention relates to a surgical instrument for removing bone, cartilage or similar material with a shaft that extends in a longitudinal direction, which at its distal end carries a cutting plate, inclined perpendicularly or relative to the longitudinal direction, with a cutting element which is movably mounted on the shaft, said cutting element supporting at its distal end a blade pointing in the direction of the cutting plate and movable towards the cutting plate in order to cut tissue.

BACKGROUND

In surgery, surgical instruments of the type described in the introduction are often used in the form of bone punches. Depending on the size of the section of tissue to be removed various instruments with appropriately dimensioned shafts and cutting elements are employed. Therefore, several instruments have to be provided for one surgical procedure. It can also happen that the instrument becomes soiled in the area between the blade and the cutting plate during an operation and has to be cleaned. The surgeon must then put the instrument aside and continue working with another instrument.

SUMMARY

It is therefore the aim of the present invention to improve a surgical instrument of the type described in the introductory section in such a way that a surgeon can quickly, easily and safely switch between different instruments.

In accordance with the invention this aim is achieved in a surgical instrument of the above type in that at the proximal end of the shaft a first coupling element is arranged for removable, positive connection with a driving device, which has a second coupling element which acts together with the first coupling element and in that the first coupling element is a polyhedron, the external surfaces of which point radially outwards from a longitudinal axis of the shaft.

The further development of known surgical instruments of the above type in accordance with the invention allows the instrument to be separated from the driving device so that only one single driving device is required for different instruments. This allows, for example, an operator to continue holding the driving device in his/her hand while an assistant detaches the instrument from the driving device and connects another instrument, which the operator needs, to the driving device. In this way a soiled instrument can also be easily and safely detached from the driving device and replaced with a clean one. By designing the first coupling element as a polyhedron rapid and secure connection of the instrument to the driving device is possible. More particularly, torsion-proof and precise positioning of the instrument on the driving device is assured. Screwing the instrument to secure it on the driving device is also not necessary as a result of which the instrument can be quickly and simply detached from the driving device and reconnected with it. The design of the first coupling element in the form of a polyhedron also ensures that only instruments permitted to be used in connection with the driving device can be connected thereto. In addition, a symmetrically designed polyhedron also allows the instrument to be arranged on and connected to the drive device in a multiplicity of different rotational positions corresponding to the number of external surfaces of the polyhedron. In this way discrete positions of the instrument relative to the drive device can be precisely predetermined.

The assembly of the instrument is particularly simple if the polyhedron is a square, a hexagon or an octagon. A square, for example, can be secured in a torsion-proof manner in four different angular positions relative to the drive device, whereby the angular positions are each at 90° to one another. In the same way with a hexagon six separate angular positions of the instrument relative to the drive device can be determined each at 60° to one another. With an octagon a total of eight angular positions at 45° to one another can be defined, namely starting at a 0° position a 45°, 90°, 135°, 180°, 225°, 270° and 315° position.

The assembly of the instrument is simplified overall and the connection of the instrument to the driving device facilitated if the proximal end of the shaft has an axis of symmetry parallel to the longitudinal direction.

If is advantageous if the shaft is sleeve-like at its proximal end and if the cutting element intersperses the sleeve-like end of the shaft. In this way a guide for the cutting element can be easily produced on the shaft.

In order to bring about axial fixing of the shaft on the driving device in a simple manner, it is beneficial if stops acting in the longitudinal direction of the shaft are provided on the first coupling element.

In accordance with a preferred embodiment of the invention it can be envisaged that a stop acting in the distal direction is arranged on the proximal side of the first coupling element and that a stop acting in the proximal direction is arranged on the distal side of the first coupling. Such an arrangement allows the second coupling element to be introduced between the two stops in the direction of the first coupling element.

In an alternative form of embodiment of the invention it can be envisaged that a stop acting in the distal direction is arranged on the distal side of the first coupling element and that a stop acting in the proximal direction is arranged on the proximal side of the first coupling element. More particularly with such an arrangement the second coupling element can positively encompass the first coupling element, namely in the longitudinal direction of the instrument.

Advantageously the polyhedron is designed in the form of a radial projection extending circumferentially. This simplifies the assembly of the instrument and, in particular, the stops acting in the distal and proximal direction are integrated on the distal and proximal sides of the first coupling element.

It is advantageous if the proximal end of the shaft has a groove, open outwards radially and extending circumferentially, with a groove base and groove side walls in the distal and proximal direction, and if the groove base forms the first coupling element. More particularly, the side walls of the groove can serve as stops acting in the distal and proximal direction. This also results in a particularly simple structure of the instrument.

It is advantageous if the proximal end of the shaft has at least one opening, extending in the radial direction, if the cutting element has at least one recess pointing in the radial direction and if in the open position of the instrument, in which the blade is at distance from the cutting plate, the opening and the recess at least partially overlap each other. In this way an open position of the instrument can be secured, for example by introducing a securing element through the opening into the recess. In this way it can be prevented that in the event of operating the driving device the instrument is moved into a closed setting in which the blade adjoins the cutting plate. Such securing or locking of the open position is particularly beneficial for cleaning purposes so that injury to a person cleaning the instrument can be ruled out.

The assembly of the instrument becomes particularly simple if the opening is a bored hole and the recess is a pocket hole, a pocket hole-like elongated hole or an annular groove.

In order to achieve definitive locking or securing of the instrument it is beneficial if a diameter of the bored hole and a width of the annular groove or a diameter of the pocket hole correspond or essentially correspond and if the bored hole and the annular groove or the pocket hole can overlap in the open position.

Advantageously the opening is arranged adjacent to the first coupling element. Such an arrangement allows one operator to hold the driving device while a second person secures the instrument in the open position and detaches the instrument in the open position from the driving device or cleans the distal areas of the instrument between the blade and the cutting plate. Accidental operation of the driving device by the operator cannot therefore result in the blade being moved against the cutting plate and the instrument thereby injuring the person who is carrying out replacement or cleaning.

So that the opening is easily accessible for a person assisting the operator, it is beneficial if the opening is arranged on the distal side of the coupling element.

In order to simplify the assembly of the instrument even further and in order to create a connection with the driving device in a simple manner, it is advantageous if at its proximal end the cutting element has a third coupling element, connected in a detachable manner to a drive element of the driving device and if stops acting in the longitudinal direction of the shaft adjoin the third coupling element. Such an arrangement allows, in particular, the drive element, for example a catch of the driving device, to engage between the stops or encompass them in order to transmit a drive force of the driving device both in the proximal and distal direction parallel to the longitudinal direction to the cutting element.

It is advantageous if a stop acting in the distal direction is arranged on the proximal side of the third coupling element and if a stop acting in the proximal direction is arranged on the distal side of the first coupling element. This simplifies operation of the cutting element as a catch can in this way engage between the two stops.

In accordance with a further preferred embodiment of the invention it can be envisaged that a stop acting in the distal direction is arranged on the distal side of the third coupling element and that a stop acting in the proximal direction is arranged on the proximal side of the first coupling element. For example the drive element can thus encompass the third coupling element on the distal side and proximal side. However, it is also conceivable for a third coupling element designed as a catch to engage between stops of the driving element acting in the distal and proximal direction.

Fundamentally it is conceivable and also advantageous for the third coupling element to be cylindrical and have a round cross-section. It could also have an elliptical cross-section. However, the assembly of the instrument is facilitated if the third coupling is a polyhedron. In particular it is beneficial if the third coupling element is designed similarly to the first coupling element.

In order to be able to detach tissue in a defined manner it is advantageous if the blade is an annularly closed blade. For example it can be circular or quadrilateral.

In order to prevent tissue removed with the instrument becoming distributed in an undesirable manner in the area of an operation site, it is beneficial if the cutting element has a cut material recess extending proximally from the its distal end for taking up removed tissue and if the blade at least partially covers an opening in the cut material recess. If tissue is removed by moving the blade towards the cutting plate, through the design in accordance with the invention it is moved directly into cut material recess and stored therein. The cut material recess therefore acts as a type of tissue or bone store for removed tissue or removed bone.

In accordance with a further preferred embodiment of the invention it can be envisaged that the cutting material recess is in the form of a pocket hole and that an movable ejector is provided in the longitudinal direction on the cutting element which from a retracted position in which it clears the cut material recess it can be moved to an ejection position in which is completely or essentially completely fills the cut material recess and vice-versa. With the ejector the cut material recess can be simply and safely emptied when it is partially or completely filled with removed tissue. Here it is conceivable for the ejector to be operated by the driving device or to be operated by itself on the instrument. By moving the ejector removed tissue and bone can be moved in the distal direction and be pushed out through the opening of the cut material recess.

An ejector can be dispensed with if a proximal end of the cut material recess is provided with a lateral ejection opening. Removed material is pushed through the opening of the cut material recess into it, but can when the cut material recess is completely full be pushed out laterally through ejection opening through the subsequent pushing of additionally removed material, thus, for example an ejector can also be introduced though the ejection opening and the material contained in the cut material recess pushed out through the distal opening.

So that an operator or a person assisting him/her can easily recognise when the cut material recess is full and may have to be emptied, it is advantageous if the cutting element has at least one viewing opening in the area of the cut material recess. Depending on the shape of the viewing opening the filling level of the cut material recess can be directly seen.

So that no removed material can emerge through the viewing opening it is advantageous for the viewing opening to be of a width perpendicular to the longitudinal direction that is smaller than the internal diameter of the cut material recess.

In order to achieve maximum stability of the instrument if a viewing opening is present, it is beneficial for several elongated hole-type viewing openings to be provided.

In order to at least determined when the cut material recess is almost filled and in order to make the instrument as stable as possible, it is advantageous if the at least one viewing opening is arranged on the distal side adjacent to the proximal end of the cut material recess.

Advantageously a guide is provided to guide a movement of the cutting element relative to the shaft in the longitudinal direction. In this way the stability of the instrument is increased, in particular if large forces are acting on the cutting element.

In order to achieve as long an instrument service life as possible it is advantageous if the blade and/or the cutting plate are provided with an abrasion-resistant coating.

A particularly long instrument service life is achieved it the abrasion-resistant coating is titanium nitride (TiN) or contains titanium nitride (TiN).

In accordance with a preferred form of embodiment of the invention it can be envisaged that provided on the shaft is a coding unit acting in conjunction with a decoding unit of the driving device in order to code the nature or type of the cutting element. The coding can be used to identify the nature or type of shaft. This has the advantage that with the driving device only those drive forces can be transmitted to the cutting element that are permitted in accordance with the nature and type of the cutting element and/or shaft. Also, this ensures that only surgical instruments intended for a particular driving device can be attached to the driving device.

Assembly of the coding unit is particularly simple if it surrounds at least one projection projecting from the shaft. Depending on the number of instruments to be coded, one or more projections can be arranged at particular positions on the shaft.

It is advantageous if a surgical instrument of the type described above or one of the above-described instruments has a driving device positively connectable in a detachable manner to the shaft and the cutting element with a drive unit for producing a drive force in a drive direction, which has a second coupling element acting in conjunction with the first coupling element. The driving device can be manually operated or by means of a mechanical or electromechanical drive. In addition, the shaft and the cutting element can be simply detached from the driving device and reconnected to the driving device.

The assembly of the instrument is particularly simple and compact if the drive unit is a fluid-driven driving unit, if the drive direction is not parallel to the longitudinal direction and if the driving device has a force deflecting unit to deflect the drive force acting in the drive direction into an operating force acting in the longitudinal direction on the cutting element. For example, in this way the driving unit can be integrated into a handle of the driving unit, which is orientated projecting laterally or perpendicularly to the longitudinal direction. This shortens one structural length of the instrument with the driving drive compared to known instruments with a driving device.

Advantageously the driving device is orientated perpendicularly or essentially perpendicularly or inclined to the longitudinal direction. This allows the driving unit to be arranged, for example in a handle area of the driving device provided projecting perpendicularly or essentially perpendicularly or inclined to the longitudinal direction.

It is beneficial if the driving unit is a fluid-operated driving unit, if the drive direction is offset laterally parallel to the longitudinal direction and if the driving unit has a force deflecting unit for deflecting the drive force acting in the drive direction into an operating force acting in a longitudinal direction on the cutting element. In this way a particularly slim structural form of the instrument is achieved as, for example, the driving unit comprising at least one fluid cylinder can be arranged parallel and laterally offset to the longitudinal axis of the shaft. By way of the force deflecting unit the drive force produced parallel to the longitudinal axis of the shaft by the driving unit can be deflected in the direction of the longitudinal axis of the cutting element.

The instrument can manage entirely without an energy supply if the driving unit comprises at least one fluid cylinder. By filling the fluid cylinder with a fluid, a piston of the fluid cylinder can be moved in a defined manner in parallel to its longitudinal axis. Overall this results in a particularly simple construction of the instrument.

In order to allow a drive force in opposing directions it is advantageous if the at least one fluid cylinder is a dual-acting fluid cylinder. In this way the cutting element can be moved in the distal and also proximal direction with a single fluid cylinder.

Advantageously the at least one fluid cylinder is a pneumatic or hydraulic cylinder. A pneumatic cylinder can be acted upon by compressed air in order to generate a drive force. A hydraulic cylinder can be operated with a fluid that can be tolerated by the body.

In accordance with a preferred embodiment of the invention it can be envisaged that the force deflection unit comprises or forms a gearing up/gearing down unit for the drive force to generate an operating force equal to a multiple corresponding to a gearing-up/gearing down ratio of the gearing-up/gearing down unit. Particularly in the case of given dimensions of the driving unit a greater driving force can be simply produced.

The assembly of the instrument becomes particularly simple if the force deflecting unit comprises an angle lever, if the angle lever has a first and a second, angled relative to the first, lever arm, if the angle lever can be pivoted in the transition area of the two lever arms on the fixed part of the driving device relative to the shaft, if the driving unit acts in conjunction with a free end of the first lever arm and if the free end of the second lever arm acts together with the cutting element. By way of this simple mechanical design a drive force acting in the drive direction can be deflected into the longitudinal direction of the instrument.

Force transmission from the driving unit to the cutting element and an interaction between the two is made particularly simple if the second lever arm bears a catch acting in conjunction with the proximal end of the cutting element.

It is advantageous if the free end of the second lever arm engages between the stop arranged on the proximal side of the third coupling element and acting in the distal direction and the stop arranged on the distal side of the third coupling element and acting in the proximal direction. A pivoting movement of the angle lever back and forth can thus be easily converted into a forward and backward movement of the cutting element. Preferably the free end of the second lever arm engages between the two stops in such a way that is does not project laterally. In this way it is practically flush perpendicularly to the longitudinal direction so that a particularly compact design is achieved in the connection area between the angle lever and the third coupling element.

It can also be advantageous if the free end of the second lever arm engages the third coupling element on the distal side acting in the proximal direction and on the proximal side acting in the distal direction. Such an arrangement is particularly suitable if the third coupling element is designed as a catch.

The transmission unit is particularly simple in design if the two lever arms of the angle lever are of different lengths. Forces can then stepped up or also stepped down in accordance with the length of the two lever arms.

Advantageously a ratio of the length of the first lever arm to the length of the second lever arm is at least 2:1. Preferably the length ratio is 3:1. In this way drive force can be easily doubled, more particularly tripled, i.e. the operating force acting on the cutting element is at least double, preferably triple the drive force generated by the driving unit.

The assembly of the instrument is simplified further if a free end of a piston of the at least one fluid cylinder is connected in an articulated manner with the first lever arm. In this way the number of required components of the instrument is minimised. With lever arms of different lengths the angle lever therefore acts as a force deflection and transmission unit at the same time.

The handling ability of the instrument is improved if the driving device comprises a casing, if a first part of the casing is designed in the form of a grip, if a second part of the casing is designed to take up the proximal end of the shaft and if the driving unit is arranged in a first part of the casing. The casing also protects the components of the driving device arranged therein, more particularly the drive unit.

It is advantageous if the shaft can be rotated relative to the driving device about an axis of rotation parallel to the longitudinal direction and can be reversibly stopped in any rotational position relative to the driving device. Depending on operating requirements the shaft can be brought into any rotational position and fixed which, in particular, allows upside down or lateral working with the instrument.

In order to create different forces with the driving unit, it is beneficial if two coupled, separately operable fluid cylinders are provided. With two fluid cylinders a total of four defined driving forces can be set, namely none, a first, a second and a third driving forces, whereby the first and second are generated by fluid acting on one cylinder in each case and the third by the fluid acting on both cylinders simultaneously.

In order to provide a total of four different driving forces, it is advantageous if the two fluid cylinders have different operating cross-sections.

It is beneficial if a ratio of operating cross-sections lies in a range of 4:1 to 9:1. Such an arrangement allows the cutting element with the blade to be moved towards the cutting plate with around 10 to 20 percent of the maximum force that can be generated with the driving unit. This prevents the tissue to be removed being cut through by the blade. An operator can thus move the instrument to the tissue to be removed, move the blade with about 10 to 20 percent of the maximum force of the driving unit against the tissue to be removed, and only after completed adjustment contact the tissue by applying the maximum force available from the driving unit to the cutting element.

In order to allow simple connection of the shaft to the driving device it is beneficial if the second coupling element is designed to correspond to the first coupling element on the driving device.

The assembly of the instrument is particularly simple if the second coupling comprises two, or at least two holding projections projecting from the first part of the casing in the direction of the shaft. The projections can positively or essentially positively engage in a circumferential groove of the shaft, the base of the groove being formed by the polyhedron.

In accordance with a further preferred embodiment of the invention it can be envisaged that the first part of the casing has a recess into which the proximal end of the shaft can be inserted and from which the distal end of the shaft in an inserted position, in which it is held immovably in the longitudinal direction, projects distally from the casing, that the recess has an insertion opening for inserting the distal end of the shaft in an insertion direction perpendicular to the longitudinal direction and that a cover is provided to close the insertion opening and to secure the shaft in the recess. Through this advantageous design the shaft and the cutting element can be simply and quickly connected to the driving device. In particular, it is only necessary to remove the cover from the insertion opening, to insert the proximal end of the shaft into the recess and to close the recess, i.e. the insertion opening, with the cover again. The shaft is thus on the one hand connected to the driving device and at the same time secured thereto. Laborious screwing of the shaft onto the driving device can also be dispensed with.

Particularly secure holding of the shaft in the recess is achieved by the cover being movably arranged on the casing and displaceable in the proximal direction in order to open the insertion opening. To open and close the insertion opening the cover only has to moved parallel to the longitudinal direction is the proximal or distal direction.

In accordance with a further preferred form of embodiment of the invention it can be envisaged that the cover is arranged in a pivoting manner about a pivoting axis on the casing. In this way it is possible to open the insertion opening by folding the cover away. After inserting the shaft in the recess the cover can be pivoted back into its initial position. Pivoting of the cover can also be combined with sliding, for example by guiding the cover in crank which initially only allows a translational movement of the cover and only after a certain slide path for it to be pivoted away. The pivoting movement can then be possible parallel or perpendicularly to the longitudinal direction.

It is advantageous if the pivoting axis is parallel or perpendicular to the longitudinal direction. Depending on the design of the driving device, more particularly the casing, it is advantageous to pivot the cover about a pivoting axis either parallel or perpendicularly to the longitudinal direction. In particular, if the cover is also borne in a displaceable manner, pivoting about a pivoting axis perpendicular to the longitudinal direction is advantageous as after opening of the insertion opening and pivoting of the cover the cover does not have to be at a distance from the instrument over its entire length, but only over a length shortened by the displacement path.

Particularly secure handling of the instrument is guaranteed if when the cover is open the supply or energy and/or operating agent to the driving unit is suspended. This ensures that when the cover is open movement of the third coupling element is prevented which prevents injury to a person wishing to change the shaft of the instrument. For this a mechanical, electrical or fluid-operated switching element can be provided to control a flow of energy or operating agent.

In order to prevent the driving device being able to be operated when cleaning the instrument, it is advantageous if on the driving device a securing element, corresponding to the opening and recess, is arranged to be movable perpendicularly to the longitudinal direction and in a securing setting engages in the recess and in a release setting clears the recess. The securing element allows an operator to hold the driving unit while a second person moves the securing element from the released position into the securing position so that operation of the driving device by the operator in ineffective. This ensures that a person wishing to exchange or clean the shaft connected to the driving device is not injured through accidental operation of the driving device by the operator.

So that the securing element is easily accessible for a person assisting the operator, the securing element is beneficially arranged on the first part of the casing adjacent to the second coupling element and held in the release position pretensioned by spring force. The instrument must actively be moved into the securing position by a second person. If the securing element is not operated an operator can used the driving device of the instrument in the required manner to remove tissue.

In accordance with a preferred form of embodiment of the invention it can be envisaged that the driving device has a decoding unit acting in conjunction with the coding unit to decode the nature and type of cutting element. This ensures that certain cutting elements cannot have too great an operating force applied to them. This can be achieved, for example, in that the coding unit having at least one projection mechanically operates one or more switching elements that limit the supply of energy and/or operating agent to the driving unit.

BRIEF DESCRIPTION OF THE DRAWINGS

The following description of preferred embodiment of the invention provides a more detailed explanation in conjunction with the drawing in which.

DETAILED DESCRIPTION

In FIGS. 1 to 5 a surgical instrument in accordance with the invention is shown in the form of a bone punch, which is denoted overall with reference number 10. The bone punch 10 comprises two essential components, namely a grip section 12 as well as a punching tool 14.

The punching tool 14 comprises an elongated shaft 18 extending in a longitudinal direction 16 which at its distal end bears a cutting plate 20 inclined about around 45° to the longitudinal direction 16. A proximal end of the shaft forms a coupling element 22 which is designed in the form of a elongated cuboid, quadratic in cross-section, with chamfered longitudinal edges. The coupling element 22 is provided with a opening 24 defining the longitudinal axis. Furthermore, at a slight distance from the proximal end of the shaft 18 on the coupling element 22 there is a groove-like recess 26 extending circumferentially, the base of the recess forming a square 28. It serves as a first coupling element for the rotationally stable connection of the punching tool 14 with the grip section 12. A side wall 30 of the recess 26 adjoining the square 28 on the proximal side forms a stop acting in the proximal direction.

On the distal side of the recess 26 four identical securing openings 34 are formed on the coupling element 22 which extend radially through the coupling element 22 in relation to the longitudinal axis 16 to the opening 24. The cuboid coupling element 22 also tapers in diameter distally and at its end has an essentially round sleeve-like shape.

The punching tool 14 has a punch 36 which at its distal end bears a blade 38 inclined vis-a-vis the longitudinal axis 16 by the same angle as the cutting plate 20. Over its entire length the stamp 38 essentially lies flat on a shaft surface 40 of the shaft. Proximally the stamp 36 passes through the opening 24 of the coupling element 22. In this area the stamp 36, which is otherwise essentially square in cross-section, is cylindrically formed. Adjoining the cylindrical section of the stamp 36 on the proximal side is a quadratic, plate-shaped flange 42, which on the distal side delimits a coupling square 44 and forms a stop acting in the proximal direction. Adjoining the coupling square 44, is an quadratic end plate 46, forming one end of the punch 36, which forms a stop acting in the distal direction. The flange 42 also forms a stop acting in the distal direction which contacts the proximal end of the coupling element 22 when the blade 38 is in its distal position, i.e. in contact with the cutting plate 20.

To stabilise a movement of the stamp 36 relative to the shaft 18, in addition to the guide formed by the coupling element 22 a guide groove 48 is arranged at the distal end of the shaft which increases in cross-section away from the shaft surface 40. Guided in the guide groove 48 is a guide projection 50 projecting from punch 36, which extends in the proximal direction parallel to the longitudinal axis 16 starting from the distal end of the punch 36. The guide projection 50 and the guide groove 48 essentially correspond, for example they can be of a swallowtail shape.

Starting from the blade 38 the punch 36 is provided with a pocket hole-like recess extending parallel to the longitudinal axis 16 which serves as tissue store 52 for tissue removed with the bone punch 10. Tissue 54 removed with the blade is pushed through a distal opening 56 of the tissue store 52 into it and on further removal of tissue 54 advanced proximally, i.e. in the direction of arrow A in FIG. 1. In the example of embodiment shown in the figures an emptying opening 58 is provided for emptying the tissue store 52 which is formed by an opening in the punch 16 running obliquely to the longitudinal axis 16 which creates a fluid connection between the tissue store 52 and an area surrounding the punching tool 14. Punched out tissue 54 stored in the tissue store 52 can be removed to the outside through the emptying opening 58. In an alternative embodiment of the invention, which is not shown, an ejector in the form of a rod movable parallel to the longitudinal axis 16 can be provided with which starting from the proximal end of the tissue store 52 tissue 54 stored therein can be pushed out through the opening 56 in the distal direction.

The grip section 12 of the bone punch 10 is essentially in the form of a pistol grip-like casing. It comprises elongated cuboid upper casing section extending parallel to the longitudinal axis 16 which has an opening 66 pointing in the distal direction and forms an essentially elongated, cuboid recess area 64 for the coupling element 22 of the shaft 18. Perpendicularly thereto and inclined slightly in the proximal direction a grip 62 projects from the upper casing section 60.

The upper casing section 60 comprises a sliding cover 70 which is guided parallel to the longitudinal axis 16 by way of two guides in the form of rib-like projections on both sides in longitudinal grooves on side walls 72 of the upper casing section 60 extending parallel to the longitudinal axis 16. In its most distal position the sliding cover 70 covers the holding area 64 completely and in its most proximal position it largely clears the holding area 64 so that an insertion opening is formed through which the coupling element 22 can be inserted into the holding area 64 in a direction perpendicular to the longitudinal axis 16.

In the inside of the side walls 72 there are opposite each other two facing coupling projections 72 forming a second coupling element. They are essentially in the form of flat cuboids the dimensions of which are selected so that the two coupling projections 74 can engage between the side walls 30 and 32 into the recess 26 and essential adjoin the square 28. In this way the punching tool 14 is axially fixed on the grip section 12.

Figure 1:
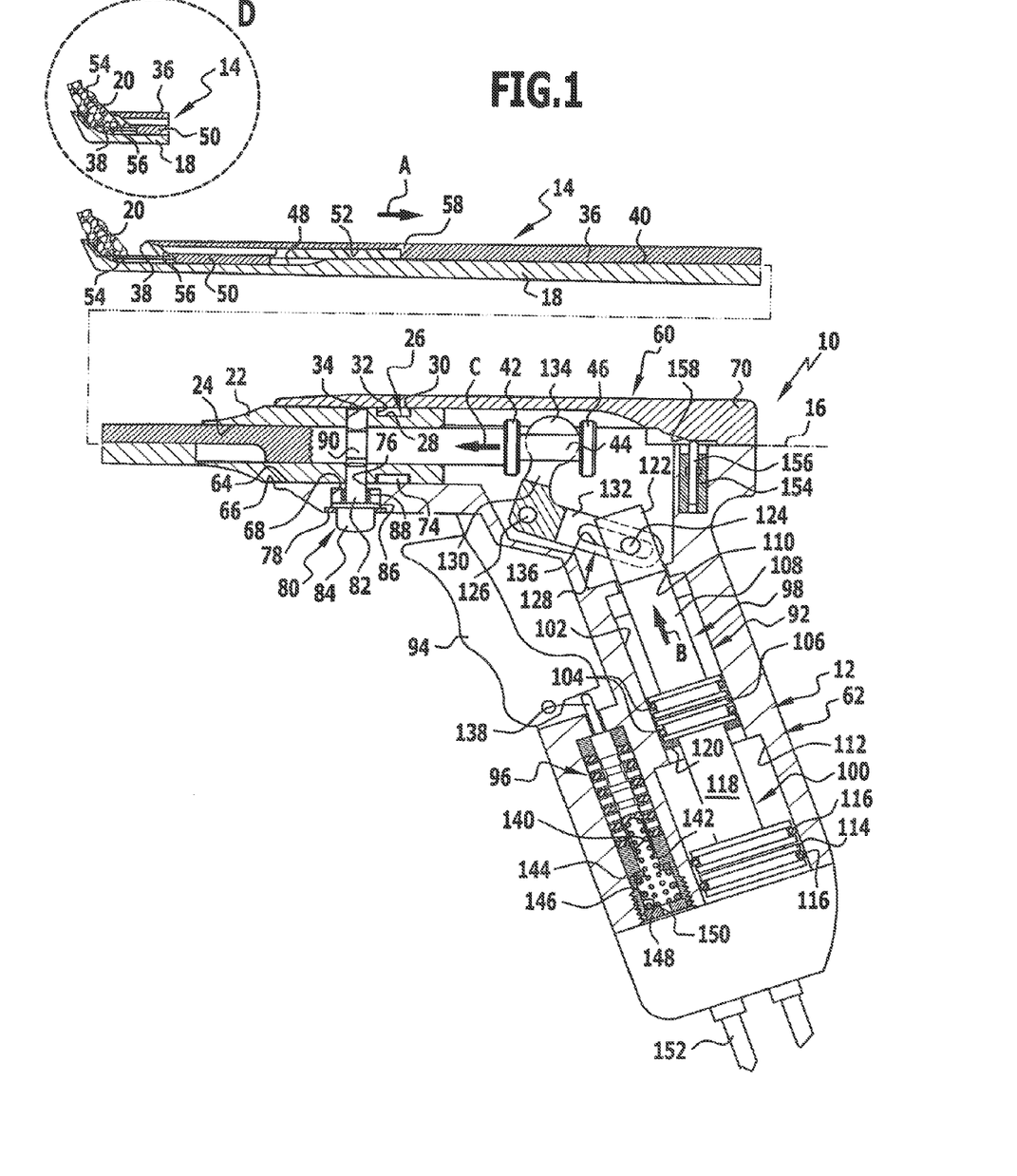
FIG. 1 shows a longitudinal section view through a bone punch in a non-operated setting

On the distal side of the coupling projections 74 the upper casing section 60 is provided on its underside with a pot-shaped recess 68, open downwards, which is connected to the holding area 64 by an opening 76. The recess 68 is provided pointing away from the holding space 64 with a disk 78 which forms a flange projecting radially inwards. The recess 68 is for a securing button 80 which comprises a cylindrical bolt 82 passing through the opening 76 and having a head 84, whereby in the transition area between the head 84 and the bolt 82 a ring flange 86 is formed that stands out radially. Adjacent to the opening 76 a coil spring 88 is supported in the recess, surrounding the bolt 82, which with its other end is in contact with underside of the head 84. In this way the ring flange 86 in a basic or rest setting is pressed against the disk 78. The securing button 80 can be moved to and fro against the action of the coil spring in the direction of the holding area 64. The securing button 80 is also arranged so that in the case of the coupling element 22 being inserted in the holding area 64 in the basic setting, in which the coil spring 88 presses the ring flange 86 against the disk 78, it essentially positively fills the securing opening 34. However, with the coupling element inserted the securing head 80 can only be moved in the direction of the holding area 64 if a punching tool 14 passing through the cylindrical section of the opening 24 overlaps the circumferentially surrounding annular groove 90 with the securing holds 34 in radial direction. As shown in FIG. 1 this is the case if the punching tool 14 is in its most proximal position relative to the shaft 18, i.e. if the distance between the blade 38 and the cutting plate 20 is at its maximum. If the securing head 80 is then pressed a forward end of the bolt 82 enters the annular groove 90 which prevents movement of the punching tool 14 parallel to the longitudinal axis 16.

A pneumatic driving device, denote as 92 overall, is essentially arranged in/on the grip 62. The driving unit 92 has on the distally facing side of the grip 62, directly below the upper casing section 60, a operating lever 94 that can be pivoted perpendicularly to the longitudinal axis 16, a switching valve 96 operable with the operating lever 94 as well as a drive unit which comprises a first pneumatic cylinder 98 and a second pneumatic cylinder 100.

The two pneumatic cylinders 98 and 100 are each dual-acting whereby the first pneumatic cylinder 98 comprises a cylindrical piston chamber 102 in a piston 106, sealed by means of two sealing rings 104, can be moved parallel to the symmetrical axis of the piston chamber 102. The piston chamber 102 is in the same way as the grip 62 slightly inclined vis-à-vis the longitudinal axis 16. Projecting from the piston 106 in the direction of the holding space 64 is a piston rod 106 which is guided in a piston boring 110 which connects the piston chamber 102 with the holder area 64. A piston chamber 112 is connected directly to piston chamber 102 with a slightly larger internal diameter. In this a moveable piston 114 is sealed by two sealing rings 116 and is connected by way of a piston rod 118 directly to the piston 106. The two pneumatic cylinders 98 and 100 thus form a rotationally symmetrical piston-cylinder unit. The piston chambers 102 and 112 are separated by a sealing ring 120 through which the piston rod 118 passes.

Attached to the piston rod 108 is a cuboid extension 122, extending in the direction of the holding area 64, which bears a drive pin 124 projecting on both sides perpendicularly to the longitudinal axis 16 and to the longitudinal axis of the piston rod 108. Running parallel to the drive pin 124 is a bearing shaft 126 in the transition area between the upper casing section 60 and the grip 62 which bears an L-shaped angle lever 128. A first lever arm 130 of the angle lever 128 essentially points in the direction of the holder area 64, a second lever arm 132 is essentially directed parallel to the holder area 64 in the proximal direction.

Free ends of the two lever arms 130 and 132 are each slit in the direction towards the bearing shaft 126 parallel to a symmetrical plane of the bone punch 10, so that the free ends are each U-shaped. The angle lever 128 is designed so that the slit free end of the first lever arm 130, which is designed as a two disk-shaped catches 134, surrounds the coupling square 44 between the flange 42 and the end plate 46 on both sides, but does not project laterally above the flange 42 and the end plate 46. The first lever arm 130 is also tapered vis-à-vis the catches so that only these can contact the flange 42 and end place 46.

The slit end of the second lever arm 132 is provided with an elongated hole-type slit 136 and surrounds the extension 122, whereby the drive pin 124 enters the slit 136 and is guided therein.

The second lever arm 132 is around twice as long as the first lever arm 130. The angle lever 128 thus forms a force deflecting unit for deflecting a drive force which can be generated in the direction of arrow B in FIG. 1 by the pneumatic cylinders 98 and 100 into a drive direction running parallel to the longitudinal axis 16 symbolised by the arrow C in FIG. 1. At the same time the angle lever 128 is also a transmission unit with which the drive force generated by the piston-cylinder unit can be doubled due to the length ratios of lever arms 130 and 132.

The pneumatic cylinders 98 and 100 are controlled by the on-off valve 96 which is arranged in parallel to the second pneumatic cylinder 100 in the area of an end of the grip 62 pointing away from the holding area 64 and has a ram 138 operable by way of operating element 94 and movable parallel to the pistons 106 and 114. Overall the on-off valve 96 is rotationally symmetrical whereby the ram 138, which passes through the on-off valve 96, is elongated and cylindrical and bears a multiplicity of annular grooves of defined depth. An end of the ram 138 pointing away from the operating element 94 is provided with a pocket hole 140 in which a coil spring 142 is supported. By way of the operating lever 94 the ram 138 can be pushed, against the action of the coil spring 142, in a direction away from the holder area 94 until it comes into contact with a disk 144 which is pressed by a second coil spring 146 against an annular wall of a cylindrical valve space 148 pointing away from the operating element 94. Both the coil spring 142 and the coil spring 146, surrounding an inlet opening 150 of the valve chamber 148 are supported on the base thereof, which points towards the operating element 94 and is opposite the annular wall. The coil spring 146 has a spring constant which exceeds that of coil spring 142 multifold. Thus, when an operator operates the operating lever 94, due to the restoring forces generated by the coil springs 142 and 146 on the ram 138 a switching position of the on-off valve 96 can be assumed. On the basis of a non-operated position of the operating lever 94 the ram 138 is initially only pressed against the coil spring 192 until the ram 138 comes into contact with the disk 144. If the operating lever 94 is moved further the ram 138 takes the disk with it and the coil spring 146 is additionally compressed. As its spring constant is many times greater than that of the coil spring 142, an operator receives a tactile acknowledgement to change to a second switching position.

The inlet opening 150 of the on-off valve 96 is connected in a manner, which is not shown, with a compressed air supply line 152, which connects the grip section 12 with a source of compressed air, which is not shown. Control inlets and outlets of the on-off valve 96, which are not shown in more detail, are connected to the two pneumatic cylinders 98 and 100 in order to implement the following function of the bone punch.

In a non-operated position of the operating lever 94 the first pneumatic cylinder 98 is supplied with compressed air in such a way that the piston 106 is moved towards the sealing disk. The bone punch then assumes its open position, i.e. the catch 134 holds the end plate 46 of the punch 36 is its most proximal position. The distance between the blade 38 and the cutting plate 20 is at a maximum.

If the operating lever 94 is moved against the coil spring 142 without the ram 138 coming into contact with the disk 144 only the piston 106 is moved by way of compressed air impingement in the direction of the arrow B in FIG. 1 between the piston 106 and the disk 120. One ratio of the effective cross-sections of the first pneumatic cylinder 98 and the second pneumatic cylinder 100 is around 1:4 so that initially only a drive force of around 20 of a maximum possible drive force is generated and transmitted via the angle lever 128 to the punch 36. The thus reduced force acting on the punch is typically not enough to cut through tissue 54 to be removed, for example bone parts. As shown in area D4 defined by the broken line in FIG. 1 the force is only sufficient to move the blade 38 to the tissue. In this first operating position of the operating element an operator of the bone punch 10 can the place the cutting plate 20 as required on the tissue 54 to be removed without cutting of the tissue 54 taking place yet.

Once the cutting position has been determined the operating lever 94 can be pushed through fully. The ram 138 is then moved against the coil spring 146 which the operator feels by the greater operating force that has to be applied in order to move the operating lever 94. The on-off valve 96 then assumes a switching position in which both the first pneumatic cylinder 98 as well as the second pneumatic cylinder 100 are supplied with compressed air, namely in such a way that both pistons 106 and 114 are moved in the direction of arrow B. Thereby a maximum driving device 92 force is transmitted via the angle lever 128 to the punch 36 which is suitable for cutting tissue 54 in the required manner.

Figure 2:
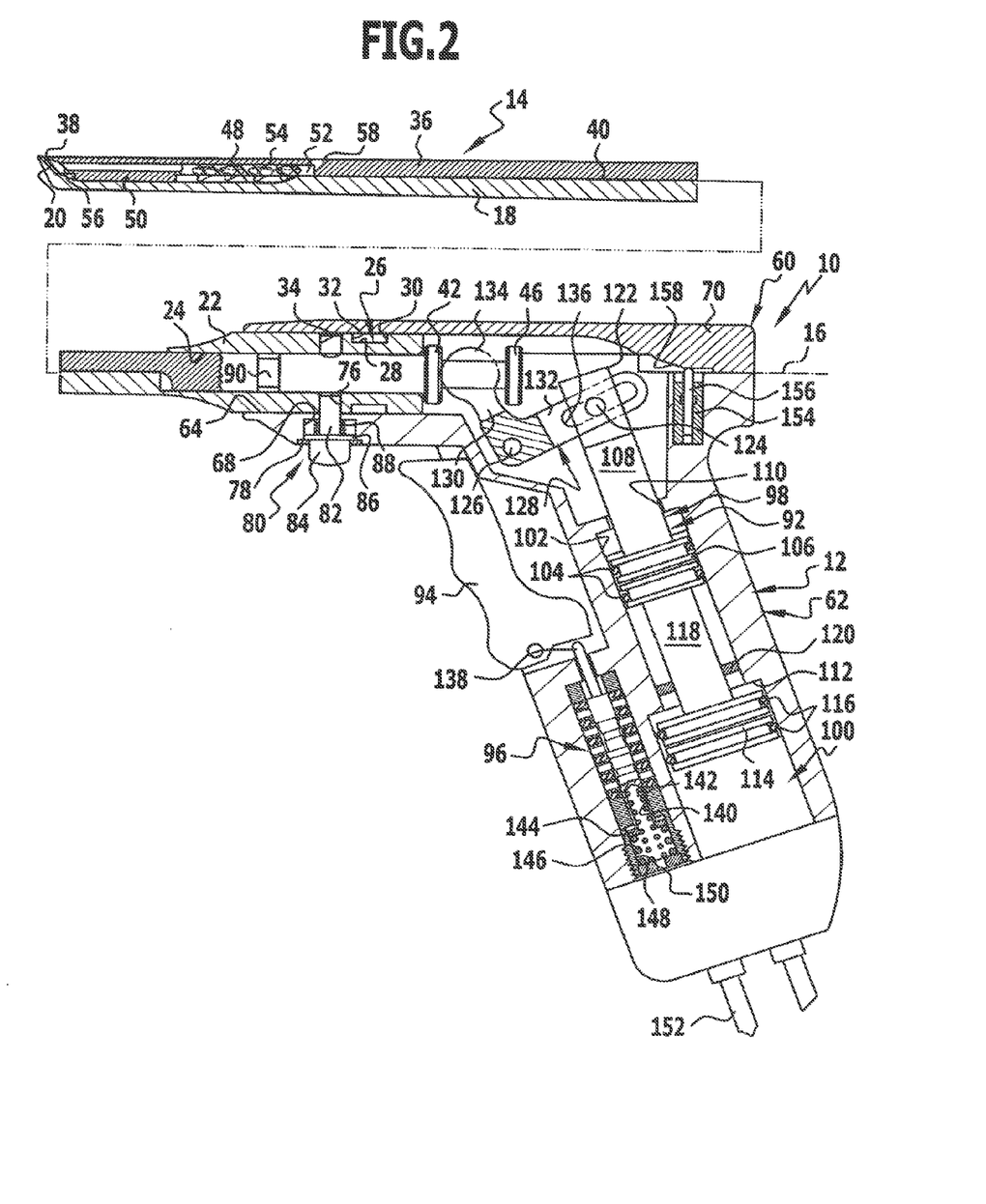
FIG. 2 shows a longitudinal section view similar to FIG. 1 in an operated setting
Figure 3:
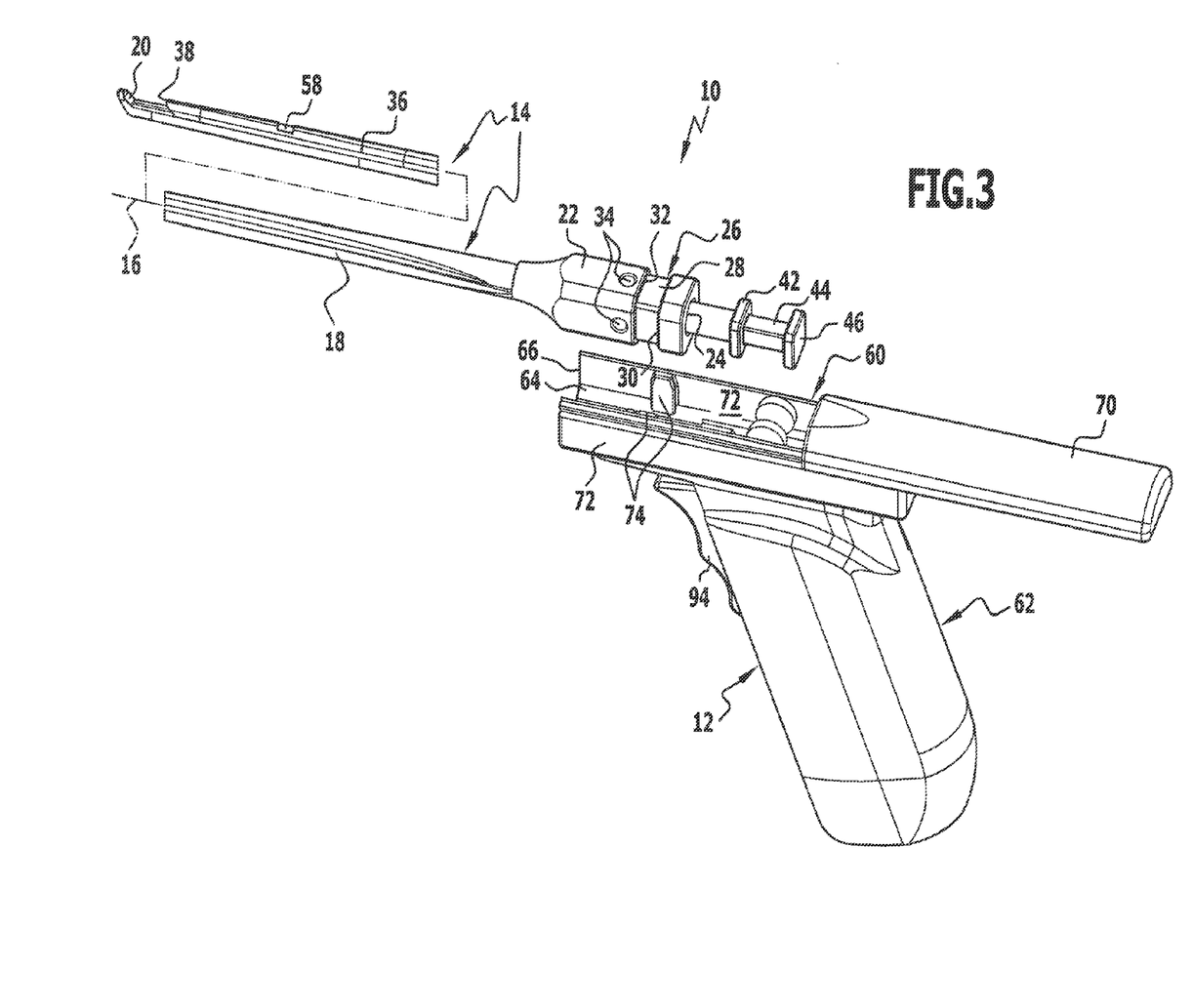
FIG. 3 shows a perspective view of the bone punch in FIG. 1 when exchanging the shaft
Figure 4:
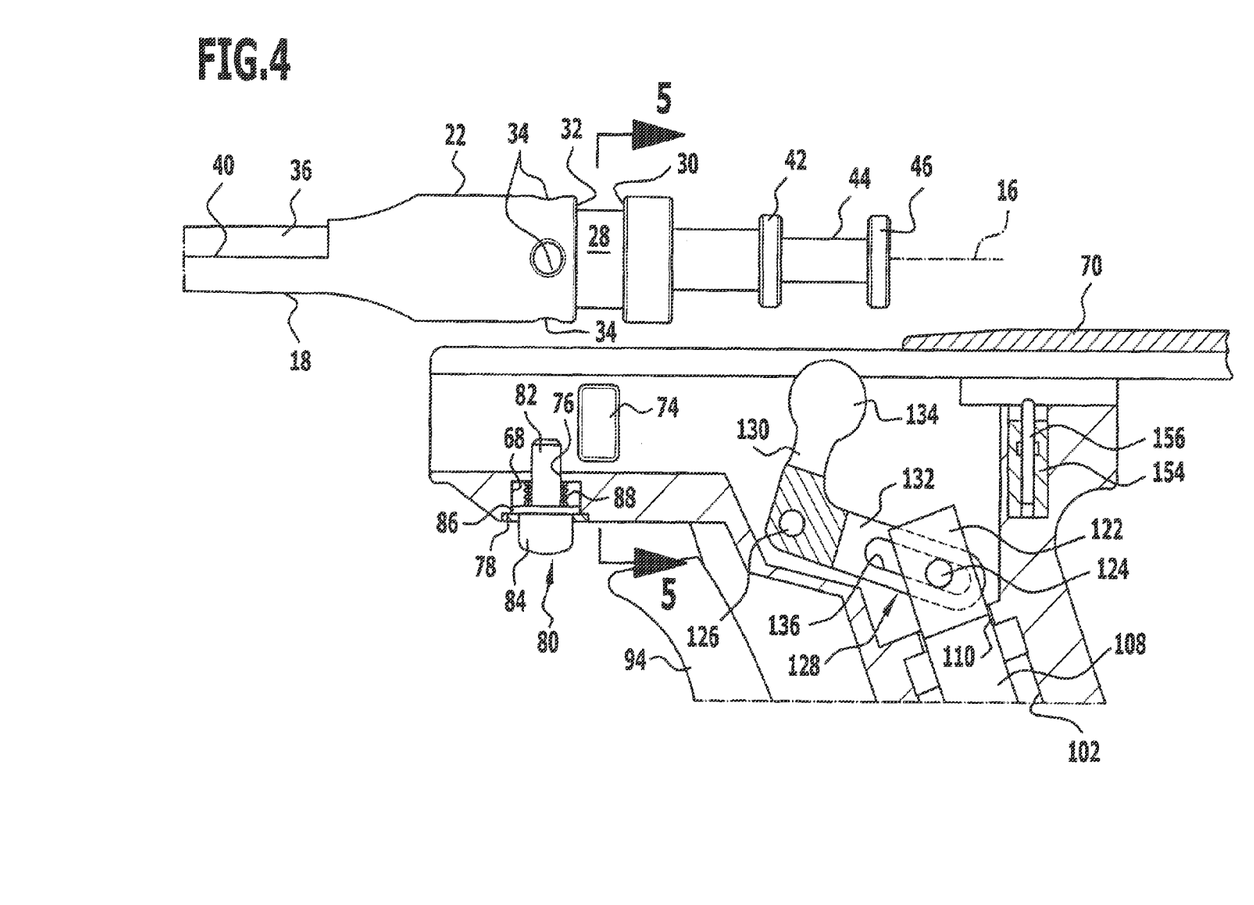
FIG. 4 shows an enlarged longitudinal section view of a shaft recess of the instrument when exchanging the shaft
Figure 5:
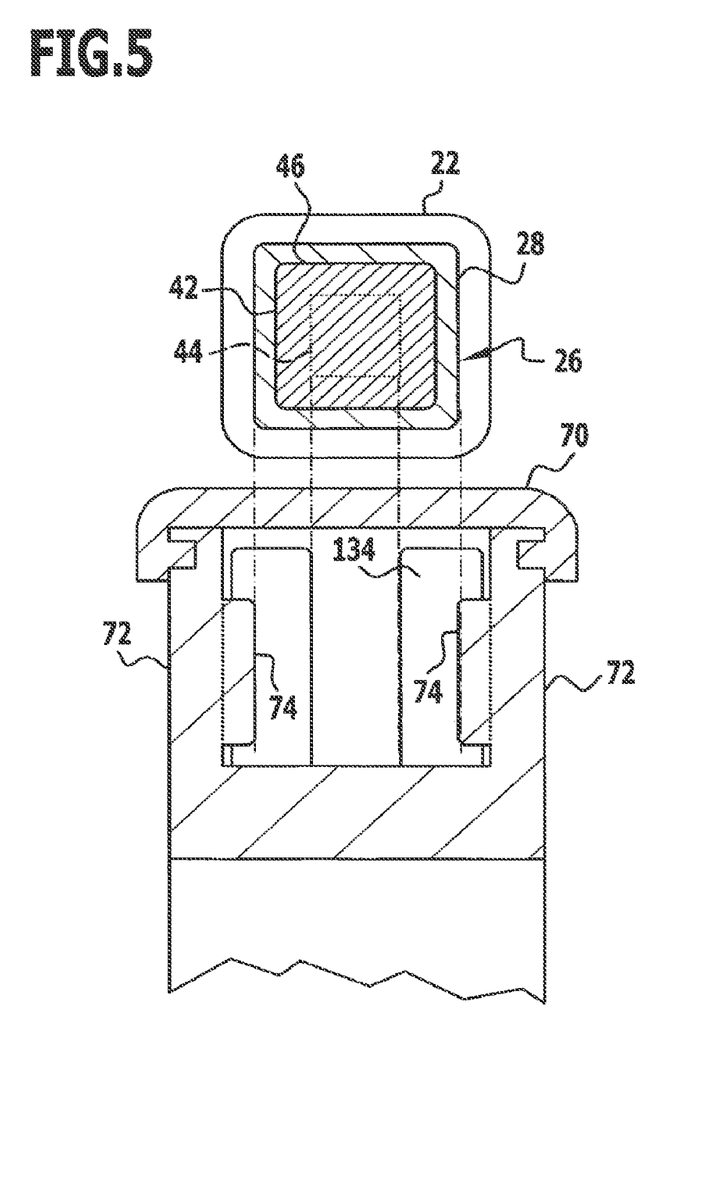
FIG. 5 shows a cross section view along line 5-5 in FIG. 4

If the operating lever 94 is released again the coil springs 142 and 146 push the ram 138 back into its initial position, the punch 36 is then forced through pressurisation of the pneumatic cylinder 98 in a direction opposite to arrow B, whereby the punch 36 is returned from its cutting position shown in FIG. 2 via its intermediate position shown in area D in FIG. 1 to its basic position shown in FIG. 1, i.e. its most proximal position.

In order to rule out accidental operation of the driving device 92 by an operator pressing the operating lever 94, a safety valve 154 is arranged in the proximal area of the upper casing section 60. The safety valve 154 comprises a valve plunger 156 arranged movably perpendicularly to the longitudinal axis 16 and pretensioned by spring force against the inside of the cover 70. If the cover closed, as shown in FIG. 1, the valve plunger 156 assumes a position in which is creates a fluid connection between the compressed air supply line 152 and the inlet opening 150 of the on-off valve 96. However, if the cover is opened the end of the valve plunger 156 projecting out of the safety valve 154 slides along an incline 158 on the inside of the cover 70 as a result of which the sprung valve plunger 156 moves further out of the safety valve 154. As a result the on-off valve 154 switches over, interrupting the connection between the compressed air supply line 152 and the inlet opening 150 of the on-off valve 96 so that operation of the operating lever 94 is ineffective as the driving device 93 is separated from the compressed air source. Only when the sliding cover 70 is completely closed again is the valve plunger 156 pushed so far into the body of the safety valve 154 that the safety valve 154 assumes its switching position again in which the compressed air supply line 152 is in fluid connection with the inlet opening 150 of the on-off valve 96.

If the bone punch 10 has to be cleaned during use, for example because tissue 54 has become jammed between the blade 38 and the cutting plate 20, an operator does not have to put the bone punch 10 down. A person assisting the operator can clean an intermediate space between the blade 38 and the cutting plate 20 without running the risk of being injured, even if the operator operates the operating lever 94. In a non-operated position of the operating lever 94 the annular groove 90 and the securing opening 34 overlap. The person assisting the operator can now press the securing button 80 against the force of the coil spring 88 so that the bolt 82 enters the annular groove 90. Movement of the punch 36 in the distal direction is prevented, even if the operator presses the operating lever 94. If the cut-off tissue 54 to be removed has been removed the person assisting the operator can release the securing button 80 again and the operator can continue the operation. The described cleaning procedure can be particularly easily carried out as the securing button 80 is arranged far enough from the operating lever 94, more particularly distally thereof, so that the securing button 80 is always freely accessible to the person assisting the operator.

Due to the special design of the coupling element 22, more particularly through the provision of the square 28, it is possible to connect the punch tool 14 to the grip section 12 in four different positions. In FIGS. 1 to 5 the punch tool 14 is connected to the grip section 12 in such a way that an intermediate space between the cutting plate 20 and the blade 38 points upwards. However, both parts of the bone punch 10 can also be connected to each other so that the intermediate space points downward or to one of the two sides of the bone punch 10. To change a relative position of the punch tool 14 to the grip section 12 the sliding cover 70 only has to be moved in the proximal direction until the holder area 63 is open and the punch tool 14 can be removed. The punch tool can then be turned about 90°, 180° or 270° and then replaced in the holder area 64. Moving the cover 70 distally closes the holder area 64 and also secures the coupling element 22 to the grip section 12.

Figure 6:
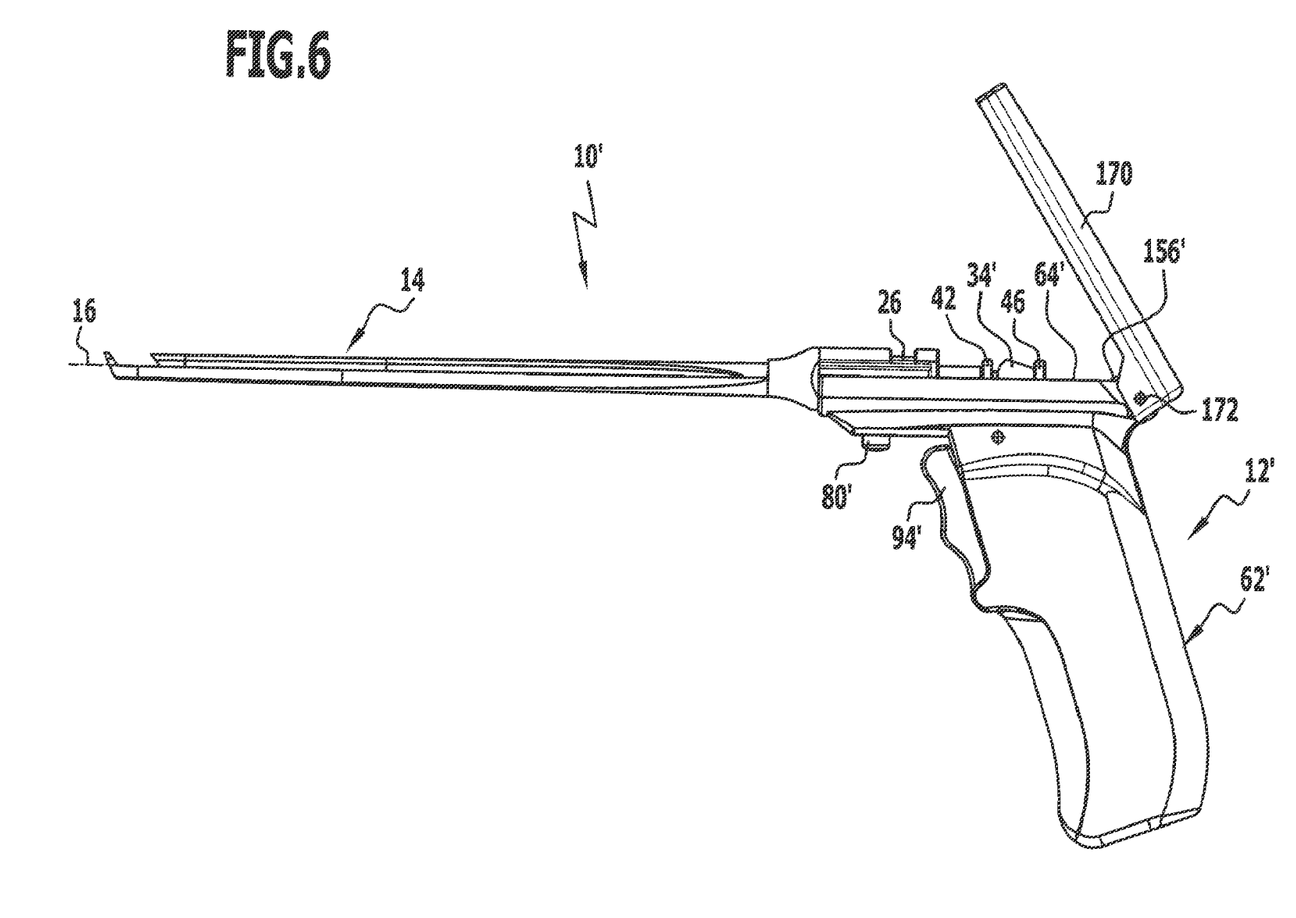
FIG. 6 shows a side view of a second embodiment of a bone punch.

In FIG. 6 a second form of embodiment 10' of a bone punch in accordance with the invention is shown in which the punch tool 14 is designed identically to the punch tool 14 of the bone punch 10, but the grip section 12' differs slightly from grip section 12 of the bone punch. Components which are designed identically in grip section 12 and grip section 12' are given the same reference numbers in the case of grip section 12' but with a superscript dash (').

The only and essential difference of grip 12' compared to grip 12 is the hinged cover 170. It is arranged at a proximal end of the holder area 64' in a pivoting manner about a pivoting axis 172 defined by two projections standing perpendicularly from the cover 170 and pointing towards each other and held in corresponding opening of the side walls 72. In FIG. 6 the hinged cover 170 is shown in its open position in which it clears the holder area 64' in order to remove the punch tool 14. By way of a lock, no shown in further detail, the hinged cover 170 can be secured its position covering and closing the holder area 64'.

Figure 7:
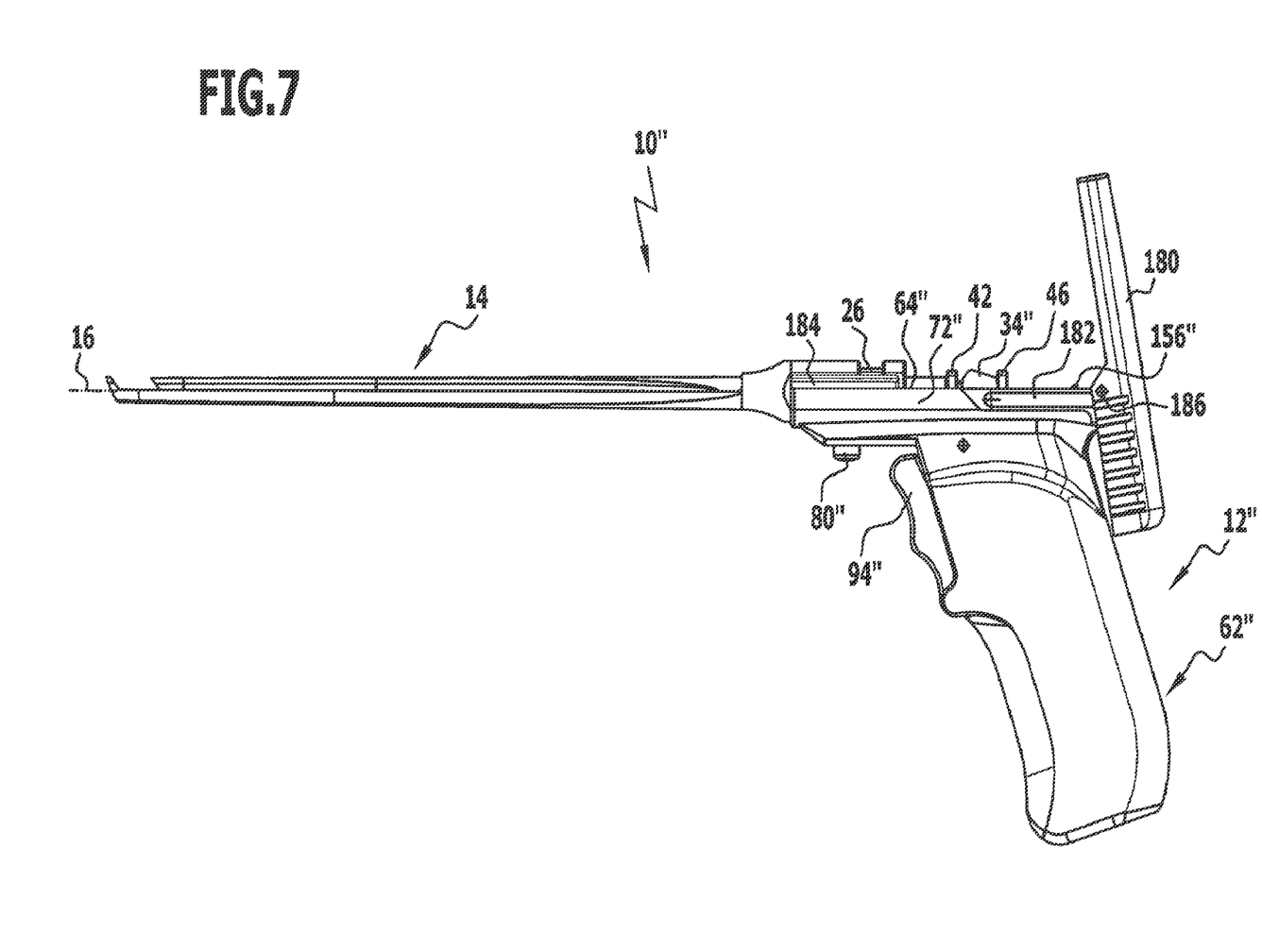
FIG. 7 shows a side view of a third form of embodiment of a bone punch.

A third example of embodiment of a bone punch in accordance with the invention is shown in FIG. 7 and denoted overall with 10". The bone punch 10" also comprises a punch tool 14 identical to the punch tool 14 of bone punch 10 as well as a grip section identified overall with 12" which differs from the grip section of the bone punch 10 through the design of the cover 180. Identical components on grip section 12 and grip section 12" are therefore given the same reference numbers with two additional superscript dashes (").

At the distal end of the side walls 72" two guide ribs 184 are arranged symmetrically on both sides of the holder area 65" which form a longitudinal guide parallel to the longitudinal axis 16 for a distal end of the cover 180. For this purposed longitudinal projections, not shown in further detail, corresponding to the two guide ribs are arranged on the cover 180. In the proximal end area of the side walls 72" these are provided with laterally open guide grooves 182 extending parallel to the guide ribs 184 into which guide projections projecting from the cover 180 in the middle and facing each other engage and thereby form a guide for the cover 118 parallel to the longitudinal axis 16.

Starting from a position, not shown, of the cover 180 closing the holder area 64", the cover can initially only be pushed in the proximal direction, namely over a stretch corresponding to the length of the guide ribs 184 on the distal end of the side walls 72". As soon as the cover 180 disengages from the guide ribs 184 it can be pivoted about a pivoting axis 186 defined by the guide projections and folded backwards in order to clear the holder area 64" completely. The punch tool 14 can now be replaced with another one. Once the other punch tool 14 has been placed in the holder area 54, to close the holder room 64" the cover 180 is initially pivoted about the pivoting axis 186 and then pushed distally parallel to the longitudinal axis 16, whereby it must be ensured that the distal end of the cover 180 engages in the guide ribs 184 again. These simultaneously form a guide and a lock for the cover 180 on the side walls 72'.

Otherwise the grip sections 12' and 12" of the bone punch 10' and 10" are identical to the grip section 12 of the bone punch 10.

The invention claimed is:

1. A surgical instrument for removing bone, cartilage or similar material with a shaft that extends in a longitudinal direction, which at its distal end carries a cutting plate, inclined perpendicularly or relative to the longitudinal direction, with a cutting element which is movably mounted on the shaft, said cutting element supporting at its distal end a blade pointing in the direction of the cutting plate and movable toward the cutting plate in order to cut tissue, wherein:
    a driving device positively connectable in a detachable manner with the shaft and the cutting element and having a drive unit for generating a driving force in a drive force direction is provided and includes a second coupling element acting in conjunction with a first coupling element arranged at the proximal end of the shaft,
    the drive unit is a fluid-operated drive unit, the drive force direction is not parallel to the longitudinal direction and the drive unit has a force deflecting unit for deflecting the drive forces acting in the drive force direction to an operating force acting in a drive direction on the cutting element,
    the force deflecting unit comprises an angle lever, the angle lever comprising a first and a second, angled relative to the first, lever arm, and
    the angle lever in the transition area between the two lever arms is pivotable on the part of the driving device fixed relative to the shaft.

2. The instrument in accordance with claim 1, wherein the second lever arm comprises a catch acting in conjunction with the proximal end of the cutting element.

3. The instrument in accordance with claim 1, wherein a free end of the second lever arm engages between a stop acting in the distal direction and arranged on the proximal side of a third coupling element and a stop acting in the proximal direction and arranged on the distal side of the third coupling element.

4. The instrument in accordance with claim 1, wherein a free end of the second lever arm comes into contact with the third coupling element on the distal side acting in the proximal direction and on the proximal side acting in the distal direction.

5. The instrument in accordance with claim 1, wherein the first and second lever arms of the angle lever are of different lengths.

6. The instrument in accordance with claim 5, wherein a ratio of the length of the first lever arm to the length of the second lever arm is at least 2:1.

7. The instrument in accordance with claim 1, wherein a free end of a piston of the at least one fluid cylinder is connected in an articulated manner with the first lever arm.

8. A surgical instrument for removing bone, cartilage or similar material with a shaft that extends in a longitudinal direction, which at its distal end carries a cutting plate, inclined perpendicularly or relative to the longitudinal direction, with a cutting element which is movably mounted on the shaft, said cutting element supporting at its distal end a blade pointing in the direction of the cutting plate and movable toward the cutting plate in order to cut tissue, wherein:
    a driving device positively connectable in a detachable manner with the shaft and the cutting element and having a drive unit for generating a driving force in a drive force direction is provided and includes a second coupling element acting in conjunction with a first coupling element arranged at the proximal end of the shaft,
    the drive unit comprises at least one fluid cylinder,
    the driving device comprises a casing, a first section of the casing is in the form of a grip, a second section of the casing is designed to hold the proximal end of the shaft and the driving unit is arranged in the first section of the casing, and
    the second coupling element comprises two holding projections projecting from the second section of the casing in the direction of the shaft.

9. A surgical instrument for removing bone, cartilage or similar material with a shaft that extends in a longitudinal direction, which at its distal end carries a cutting plate, inclined perpendicularly or relative to the longitudinal direction, with a cutting element which is movably mounted on the shaft, said cutting element supporting at its distal end a blade pointing in the direction of the cutting plate and movable toward the cutting plate in order to cut tissue, wherein:
    a driving device positively connectable in a detachable manner with the shaft and the cutting element and having a drive unit for generating a driving force in a drive force direction is provided and includes a second coupling element acting in conjunction with a first coupling element arranged at the proximal end of the shaft,
    the drive unit comprises at least one fluid cylinder,
    the driving device comprises a casing, a first section of the casing is in the form of a grip, a second section of the casing is designed to hold the proximal end of the shaft, and the driving unit is arranged in the first section of the casing, and
    the second section of the casing comprises a holding area into which the proximal end of the shaft can be inserted and from which the distal end of the shaft in an inserted position, is immovably held in the longitudinal direction, it projects in the distal direction from the casing, the holding area has an insertion opening for inserting the proximal end of the shaft in an insertion direction perpendicular to the longitudinal direction and a cover for closing the insertion opening and securing the shaft in the holding area is provided.

10. The instrument in accordance with claim 9, wherein the cover on the casing is displaceable and can be displaced in the proximal direction to open the insertion opening.

11. The instrument in accordance with claim 10, characterised wherein the cover on the casing can be pivoted about a pivoting axis.

12. The instrument in accordance with claim 11, wherein the pivoting axis is parallel or perpendicular to the longitudinal direction.

13. A surgical instrument for removing bone, cartilage or similar material with a shaft that extends in a longitudinal direction, which at its distal end carries a cutting plate, inclined perpendicularly or relative to the longitudinal direction, with a cutting element which is movably mounted on the shaft, said cutting element supporting at its distal end a blade pointing in the direction of the cutting plate and movable toward the cutting plate in order to cut tissue, wherein:
- a driving device positively connectable in a detachable manner with the shaft and the cutting element and having a drive unit for generating a driving force in a drive force direction is provided and includes a second coupling acting in conjunction with a first coupling element arranged at the proximal end of the shaft, and
- with a cover open, at least one of an energy or operating agent supply to the driving unit is interrupted.

14. A surgical instrument for removing bone, cartilage or similar material with a shaft that extends in a longitudinal direction, which at its distal end carries a cutting plate, inclined perpendicularly or relative to the longitudinal direction, with a cutting element which is movably mounted on the shaft, said cutting element supporting at its distal end a blade pointing in the direction of the cutting plate and movable toward the cutting plate in order to cut tissue, wherein:
- a driving device positively connectable in a detachable manner with the shaft and the cutting element and having a drive unit for generating a driving force in a drive force direction is provided and includes a second coupling element acting in conjunction with a first coupling element arranged at the proximal end of the shaft, and
- on the driving device a securing element corresponding to an opening and a recess is arranged movably perpendicularly to the longitudinal direction and in a securing position enters the recess and in a releasing position clears the recess.

15. The instrument in accordance with claim 14, wherein the securing element is held spring-loaded in the releasing position on the first section of a casing adjacent to the second coupling element.

* * * * *